(12) United States Patent
Timme et al.

(10) Patent No.: US 11,491,252 B1
(45) Date of Patent: Nov. 8, 2022

(54) PATHOGEN CONTAINMENT SHIELD

(71) Applicants: William F. Timme, Oradell, NJ (US); Michael S. Evangel, Ramsay, NJ (US)

(72) Inventors: William F. Timme, Oradell, NJ (US); Michael S. Evangel, Ramsay, NJ (US)

( * ) Notice: Subject to any disclaimer, the term of this patent is extended or adjusted under 35 U.S.C. 154(b) by 389 days.

(21) Appl. No.: 16/875,509

(22) Filed: May 15, 2020

(51) Int. Cl.
| | |
|---|---|
| A61L 2/10 | (2006.01) |
| A61L 2/26 | (2006.01) |
| E05G 7/00 | (2006.01) |
| A61L 2/02 | (2006.01) |

(52) U.S. Cl.
CPC ............... *A61L 2/26* (2013.01); *A61L 2/022* (2013.01); *A61L 2/10* (2013.01); *E05G 7/005* (2013.01)

(58) Field of Classification Search
CPC ... A61L 2/26; A61L 2/022; A61L 2/10; E05G 7/005
See application file for complete search history.

(56) References Cited

U.S. PATENT DOCUMENTS

| | | | | |
|---|---|---|---|---|
| 2,914,244 A * | 11/1959 | Wheeler | ............... | A47B 88/90 312/28 |
| 3,328,524 A * | 6/1967 | Bechtel | ............... | H04M 9/001 379/453 |
| 3,817,310 A * | 6/1974 | Petersen | ............... | A47F 10/06 160/369 |
| 3,847,250 A * | 11/1974 | Sherrill | ............... | A47F 10/06 186/44 |
| 3,861,119 A * | 1/1975 | Taggart | ............... | G07D 11/10 53/550 |
| 3,994,243 A * | 11/1976 | Anders | ............... | E05G 7/002 49/505 |
| 4,013,880 A * | 3/1977 | Kennedy, Jr. | ............ | A47F 10/06 248/220.21 |
| 4,892,366 A * | 1/1990 | Yerman | ............... | A47F 3/007 312/140.4 |
| 5,584,545 A * | 12/1996 | LaVaute | ............... | A47B 97/00 108/115 |
| 6,006,681 A * | 12/1999 | Brown | ............... | E05G 7/008 109/19 |
| 8,308,249 B2 * | 11/2012 | Matus, Jr. | ............... | A47F 10/06 312/137 |
| 9,364,101 B1 * | 6/2016 | Anderson | ............... | A47F 3/007 |
| 11,129,484 B2 * | 9/2021 | Scott | ............... | E06B 3/48 |
| 2003/0174292 A1 * | 9/2003 | White | ............... | G03B 21/10 353/74 |

(Continued)

*Primary Examiner* — Sean M Luck (57) ABSTRACT

A pathogen containment shield comprises a plexiglass barrier to protect both employees on the one side of the barrier from infecting or being infected by customers on the other side of the barrier. The shield includes a vertical portion with an upper outwardly extending portion and side wings extending outwardly from the vertical portion in the direction of the customer. A hood mounted to the upper outwardly extending portion and including a tourmaline and antimicrobial infused filter, a fan designed to direct droplets into the filtration box at the base of the vertical barrier. The hood also includes an auto distance sensor and programmable auto timer to activate the fans and the filtration box when a customer approaches the shield and to turn off the operation a set time after the customer leaves. The filtration box includes a removable tourmaline and antimicrobial infused intake filter and pathogen killing UV-C light.

11 Claims, 9 Drawing Sheets

(56) References Cited

U.S. PATENT DOCUMENTS

| | | | |
|---|---|---|---|
| 2004/0056201 A1* | 3/2004 | Fink | A61L 2/202 |
| | | | 250/352 |
| 2005/0061161 A1* | 3/2005 | Hunot | A47J 37/048 |
| | | | 99/441 |
| 2016/0073795 A1* | 3/2016 | Matus, Jr. | A47F 10/06 |
| | | | 312/137 |
| 2018/0089963 A1* | 3/2018 | Wallace | G07F 19/204 |
| 2020/0046146 A1* | 2/2020 | Hansen | A47F 10/06 |
| 2020/0245786 A1* | 8/2020 | Kurmlavage | A47F 10/06 |
| 2022/0092577 A1* | 3/2022 | Ahn | G07G 1/0018 |

* cited by examiner

PATHOGEN CONTAINMENT SHIELD

CROSS REFERENCE TO RELATED APPLICATIONS

Not Applicable.

STATEMENT REGARDING FEDERALLY SPONSORED RESEARCH OR DEVELOPMENT

Not Applicable.

PARTIES TO A JOINT RESEARCH AGREEMENT

Not Applicable.

DESCRIPTION

Field of the Invention

This invention relates to a containment shield for the protection of both employees and customers from pathogens and/or bacteria laden droplets as a result breathing, talking, coughing or sneezing.

Background of the Invention

This invention involves a unique shield means for protecting service personnel and customers from pathogens such as the coronavirus known as SARS-CoV-2. A pathogen can be readily spread by coughing or sneezing and is easily transmittable.

It is often difficult to determine who is infected since many carriers are asymptomatic. Consequently, is essential to protect employees and individuals who may be in contact with the public such as cashiers, postal workers, bank employees and a host of other individuals. The present invention provides a unique plexiglass containment shield shaped to contain and protect individuals from the pathogen. Incorporated within the invention are filters and a filtration device with technology known to reduce airborne pathogen in respiratory droplets and aerosols.

The prior art does include plexiglass shields but generally they permit pathogen droplets to escape over or around the shield. While it is easier and cheaper to merely use a plastic barrier; these prior art designs are less effective with a highly transmittable pathogen.

The present invention is designed to effectively protect individuals, both customers and employees who must deal with each other face to face. The containment shield proposed herein is reasonable in cost, and is significantly more effective.

SUMMARY OF THE INVENTION

This invention pertains to a shield to protect individuals at point of service from being infected by a pathogen such as SARS-CoV-2. This containment shield is designed to protect both employees and customers from pathogen laden droplets or aerosol as a result of breathing, talking, coughing or sneezing.

The device comprises a plexiglass barrier which includes a vertical portion, side portions or wings extending outwardly therefrom and an outwardly extending upper portion to surround, redirect, contain and reduce the number and concentration pathogens. This is on the customer side of the shield. The shield is generally mounted on a counter or table top and includes a filtration box mounted at the base of the vertical shield portion. The filtration box uses UV-C light, tourmaline and antimicrobial HEPA and CoolVision filters designed to reduce pathogens in the air.

A fan or vacuum means may be used in conjunction with the shield to direct droplets into the filtration box on the customer side of the shield as well as from the attendant's side of the shield. The filtration box also includes an auto distant sensor and a programmable auto timer to activate the vacuum and pathogen reducing system when a customer approaches the shield and turn off the operation after a pre-set time after the customer leaves.

Accordingly, it is an object of this invention to provide a new and improved means for shielding individuals from a contagious pathogen.

It is another object of this invention to provide a uniquely shaped plexiglass shield to protect individuals from a contagious pathogen when dealing with the public.

It is another object to this invention to provide a new and improved table top containment shield to protect employees from highly contagious pathogens carried by customers which includes a shaped plexiglass shield and means to kill pathogen droplets.

It is a more specific object to this invention to provide a uniquely shaped plexiglass shield and means to direct pathogen droplets to a filtration box which includes pathogen killing means that is automatically activated for a predetermined time interval when an individual is sensed.

BRIEF DESCRIPTION OF THE DRAWINGS

The above and other objects of this invention might be more clearly seen when viewed in conjunction with the accompanying drawings wherein.

DETAILED DESCRIPTION OF THE INVENTION

Figure 1:
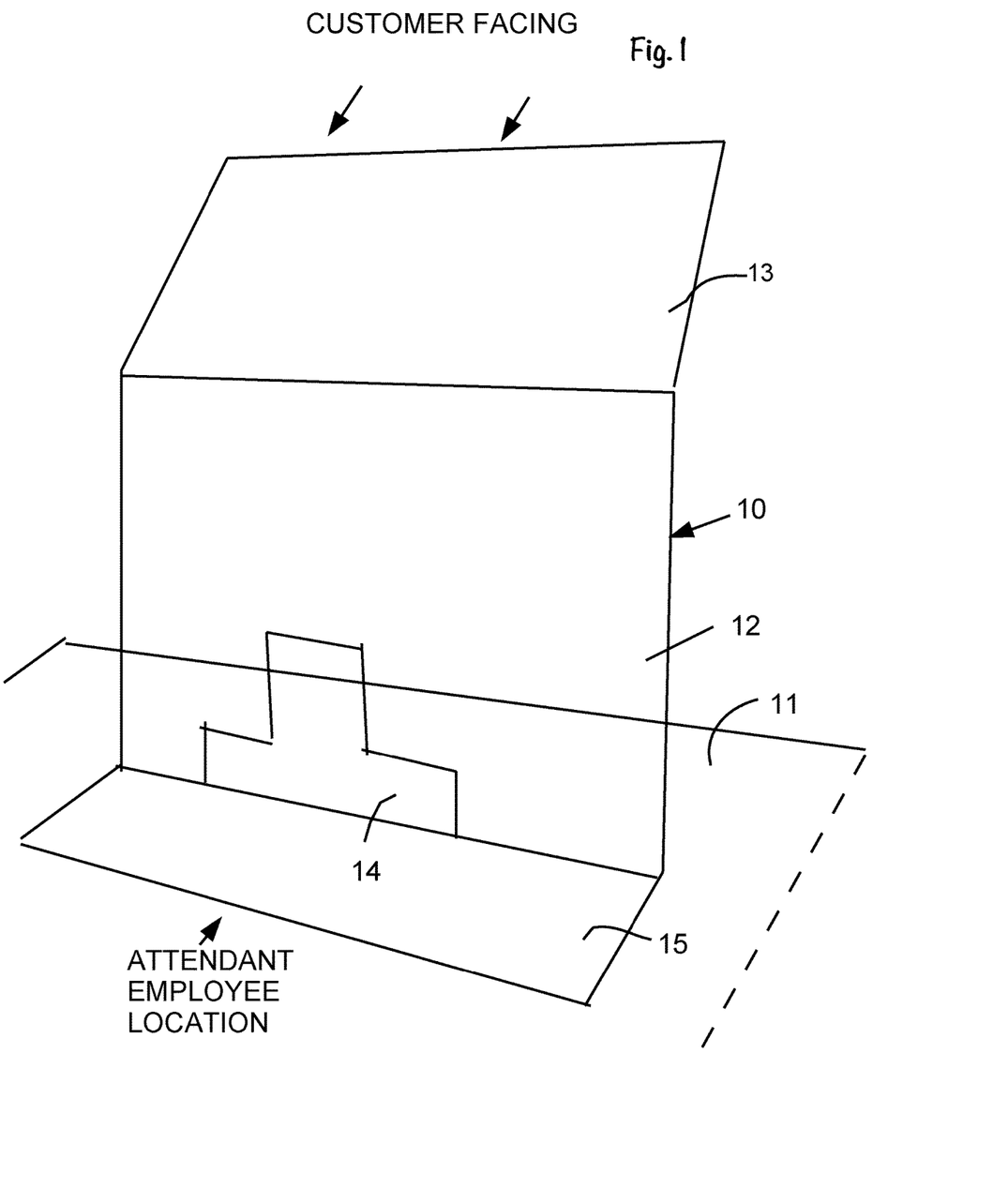
FIG. 1 is a perspective view of the basic pathogen containment shield of this invention without additional components.

Referring now to the drawings, FIG. 1 shows a basic plexiglass containment shield 10, mounted on a table top or counter 11. The shield 10 includes a vertical portion 12 having an outwardly angled upper portion 13 on the customer side of the table to protect an employee on the opposite side of the table. The lower portion of the vertical shield 12 includes a cutout slot 14 and a base 15 extending towards the employee side of the table 11 and fastened thereto. The slot 14 is T-shaped to allow for two different filtration black boxes (not shown) to be positioned therethrough, one on a vertical plane and the other on a horizontal plane.

Figure 2A:
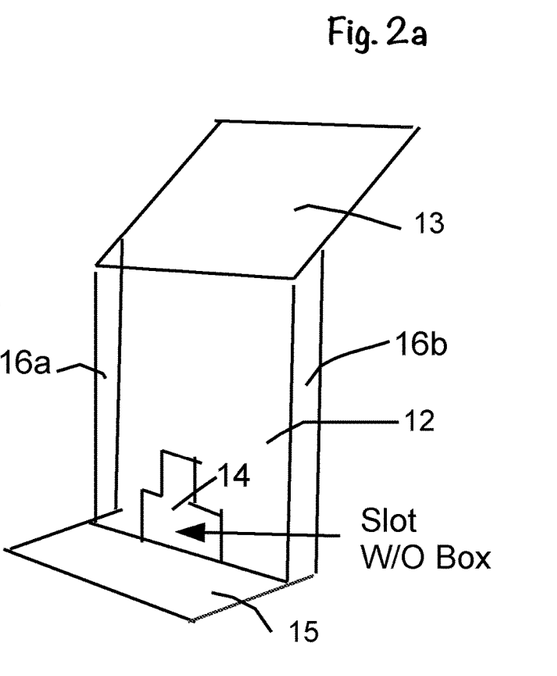
FIG. 2a is a perspective view of the droplet shield with containment wings.
Figure 2B:
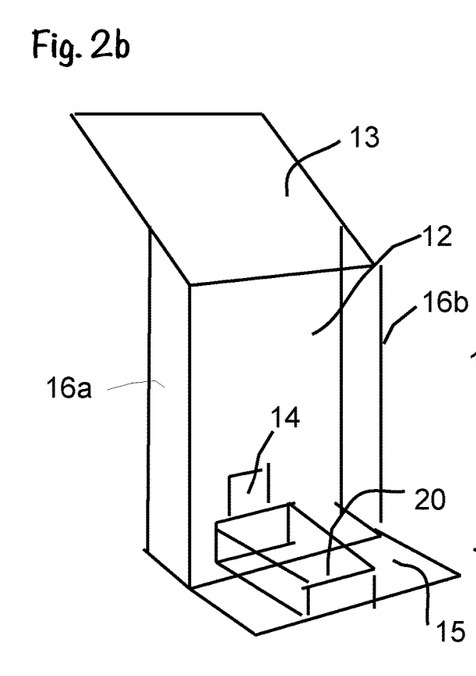
FIG. 2b is a perspective view of the droplet shield and filtration box.

FIG. 2 a and FIG. 2b depict a containment shield 10 with droplet containment wings 16a and 16b which extend outwardly from the vertical portion 12 in the customer's direction. The wings 16a and 16b engage the upper angled shield portion 13. FIG. 2b shows a filtration box 20 which engages the slot 14 so that half of the box 20 is on each side of the vertical shield portion 12.

Figure 3:
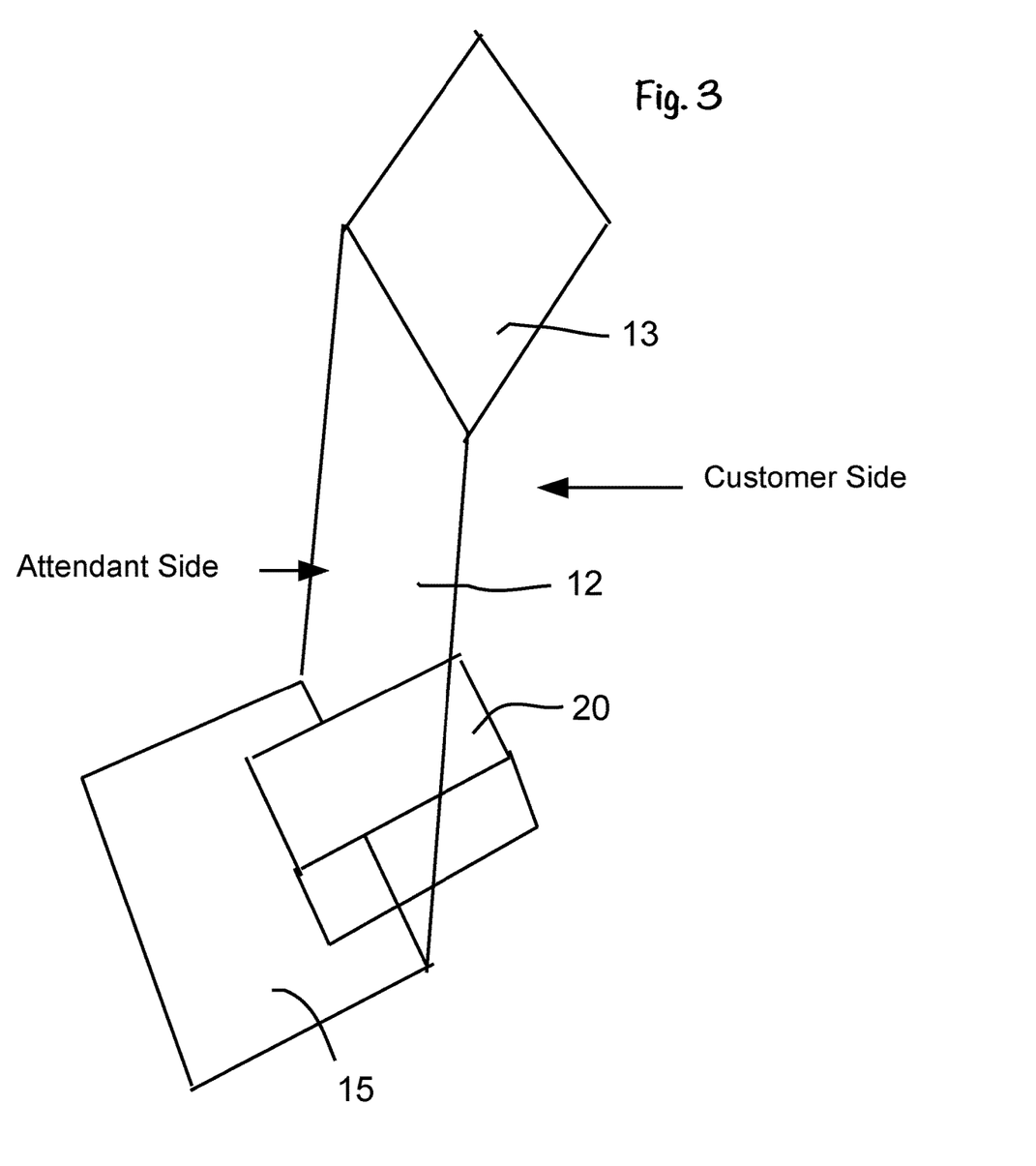
FIG. 3 Is a perspective view of a base mounted electronic component box mounted to the shield.

FIG. 3 depicts a base mounted electronic component box 20 which is attached to the shield 10 and extends through the slot 14. Half of the box 20 is on the customer side and half of the box 20 is on the attendant side. A ¼-inch plexiglass spacer 21 is used to stop the box 20 at a particular position and to elevate the box 20 to the same height as the base 15.

Figure 4:
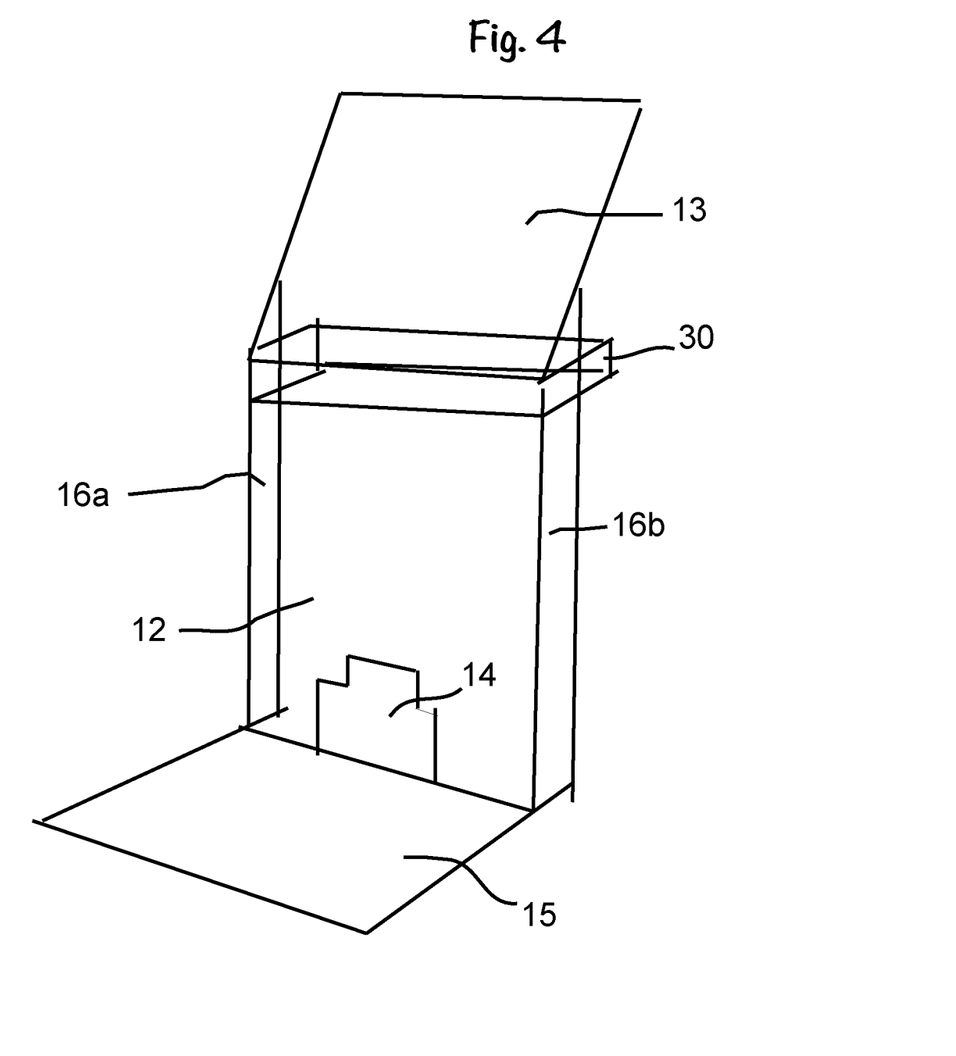
FIG. 4 Is a perspective view of the shield with deflector wings and an upper hood unit
Figure 5:
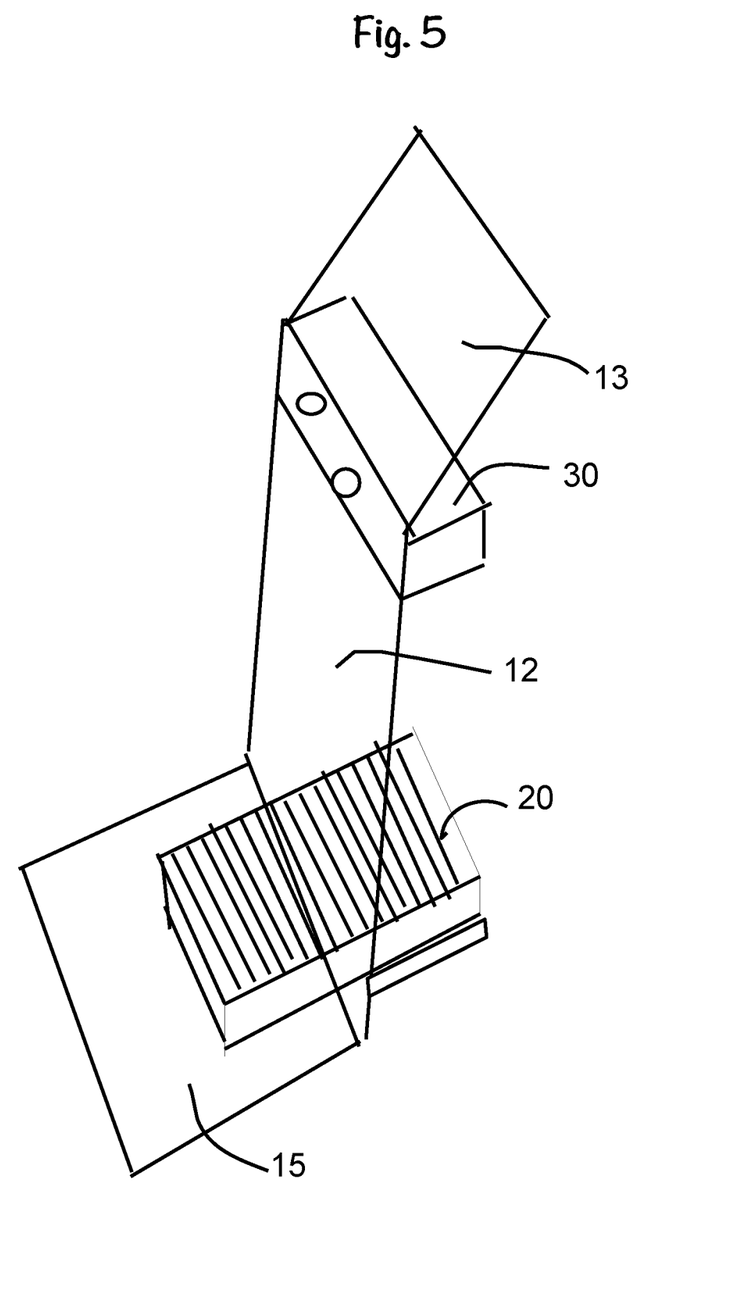
FIG. 5 is a perspective view of the shield including an upper hood unit with a draft generator to direct pathogen laden air into a filtration box.

As shown in FIG. 4 and FIG. 5, the clear vertical shield 12 with deflector wings 16a, 16 b includes an upper hood unit 30 on the customer side of the shield 10. Draft generating low speed fans 31 are mounted within the hood 30 to be activated by a motion sensor 32 when a customer is within a certain distance of the shield 10 (see FIG. 7 for more details). The hood 30 also includes a timer 33 which automatically turns off the fans 31 at a predetermined time after a customer has left the area. The purpose of the fans 31 is to direct pathogen droplets downwardly through filters 33 to the filtration electronic box 20. The outwardly extending wings 16 a, 16 b are omitted in FIG. 5 but they are preferable to limit the spread of the pathogen.

Figure 6:
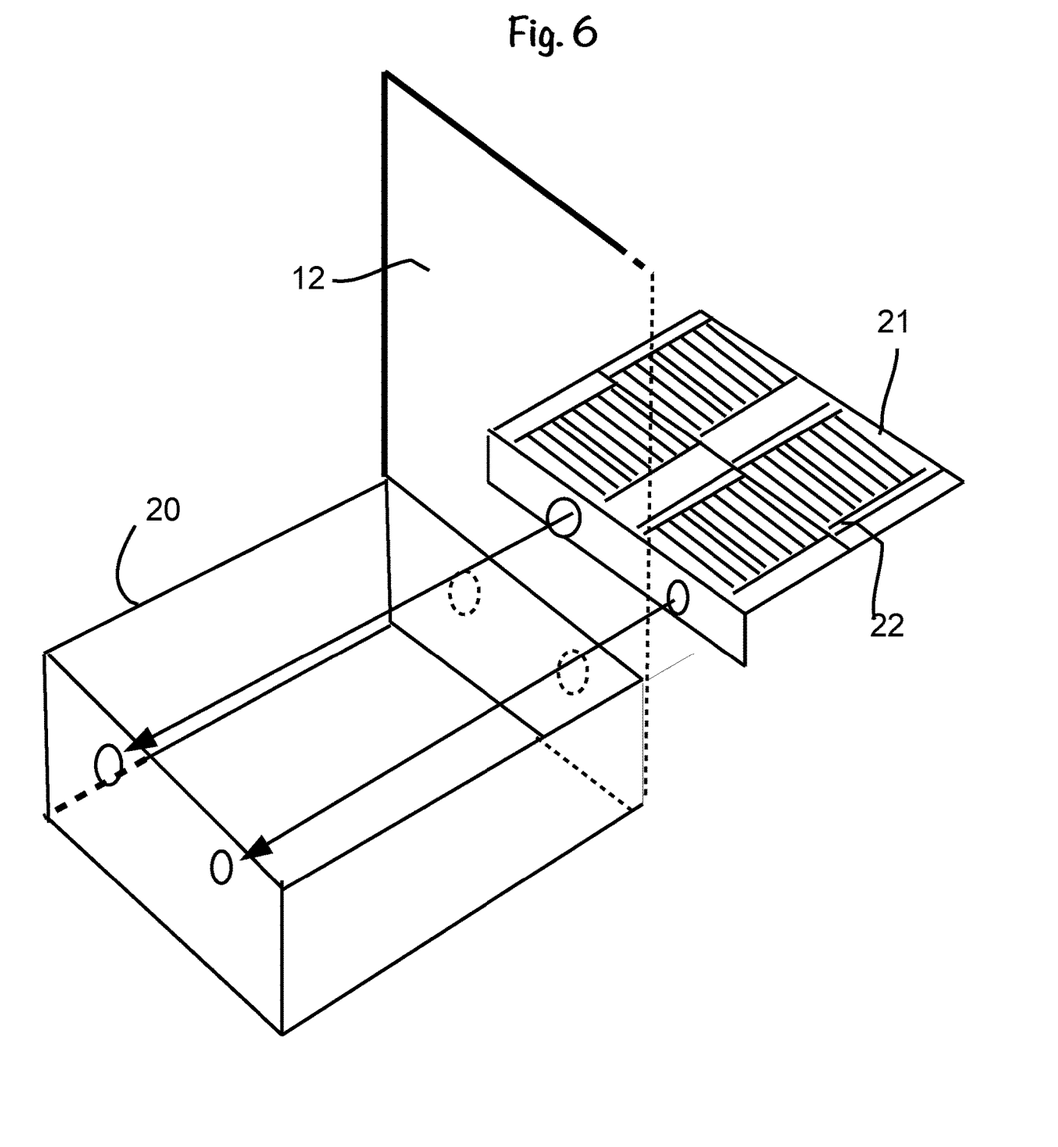
FIG. 6 is a perspective view of a base mounted electronic component box.

FIG. 6 shows the base mounted electronic component box 20 which extends through the slot 14 in the vertical shield portion 12. The box 20 includes a cover 21 with a register type input or droplet collection vent with fins 22. The base mounted box 20 is attached to the vertical shield 12 and as more particularly shown extends through the slot 14 in equal portions. The fans 31 in the hood unit 30 create enough of a downward draft to force any droplets generated by a customer through the vent 21 in the base mounted electronic box 20. The droplets are then forced to pass through a disposable and replaceable antimicrobial filter 22. The vast majority of the pathogens that are trapped in the filter will be killed by the combination of the antimicrobial in the filter and the UV-C light.

Figure 7:
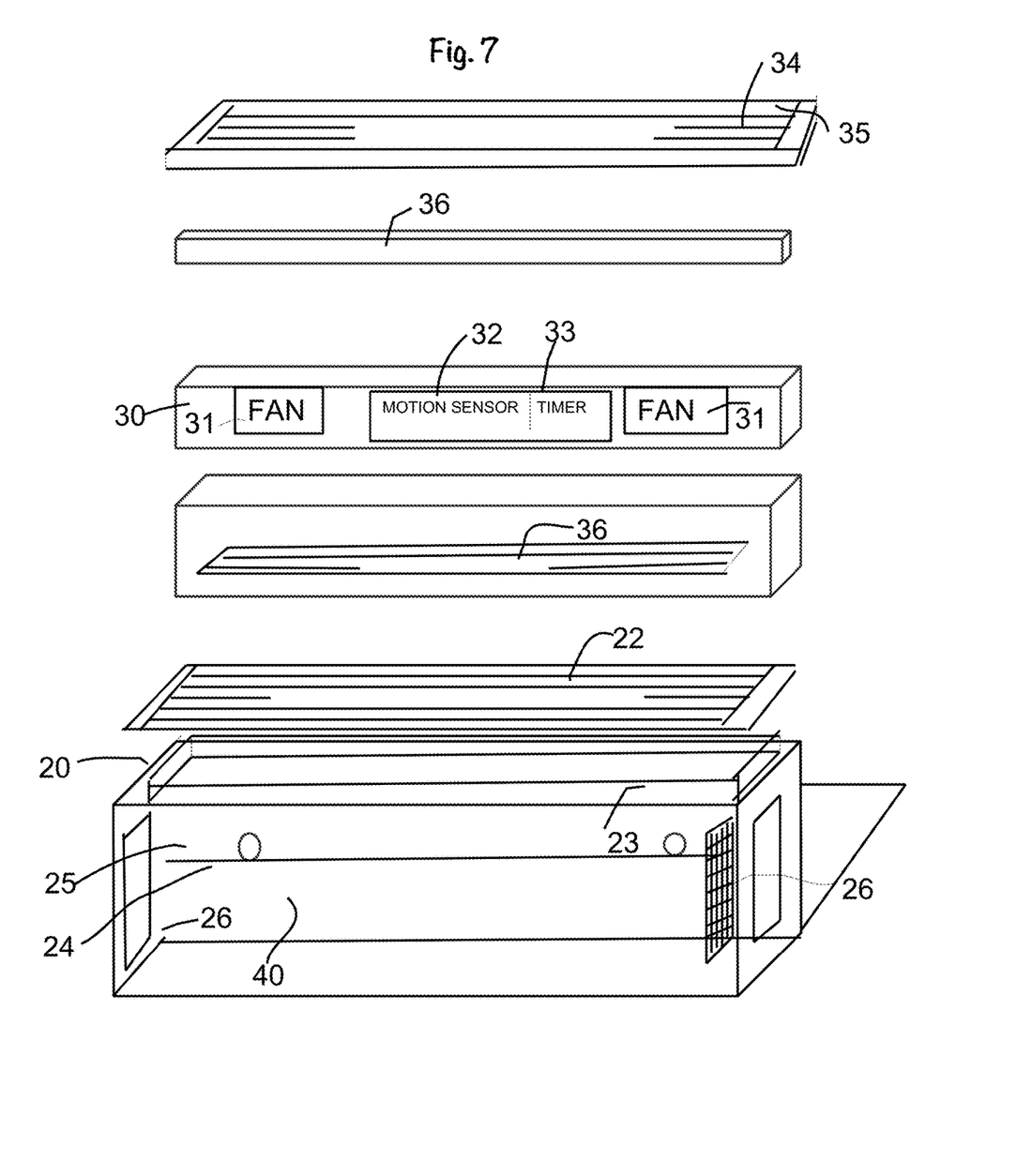
FIG. 7 is an exploded schematic view of the open hood unit and the base filtration unit.

The upper hood unit 30 and base unit 20 are shown in a stacked order in FIG. 7. The hood 30 includes an upper unit intake register 34 with fins 35 along the upper surface thereof and a removable drop in tourmaline filter 36. Below the filter 34 is a double fan 31 downward draft system with a motion sensor 32 and timer 33. The hood unit 30 terminates in an exhaust register 36 which directs the flow of air and consequently any remaining pathogen droplets downwardly to the base unit 20.

The base unit 20 includes a lower unit droplet intake register 22, a removable tourmaline intake filter 23 and a base 24 in the shape of a rectangular box. The base 24 includes vacuum means 25 and removable tourmaline intake and exhaust filtration. Exhaust filters 26 are mounted at each end of the box 24. The base box 24 also contains pathogen killing antimicrobial agents and a UV-C bulb. This two stage operation insures that if pathogen droplets are not contained in the upper hood unit 30, they are again greatly reduced by the lower unit 20 to further reduce pathogen exposure to the employee and the customer from exhaling, talking, coughing or sneezing.

Figure 8:
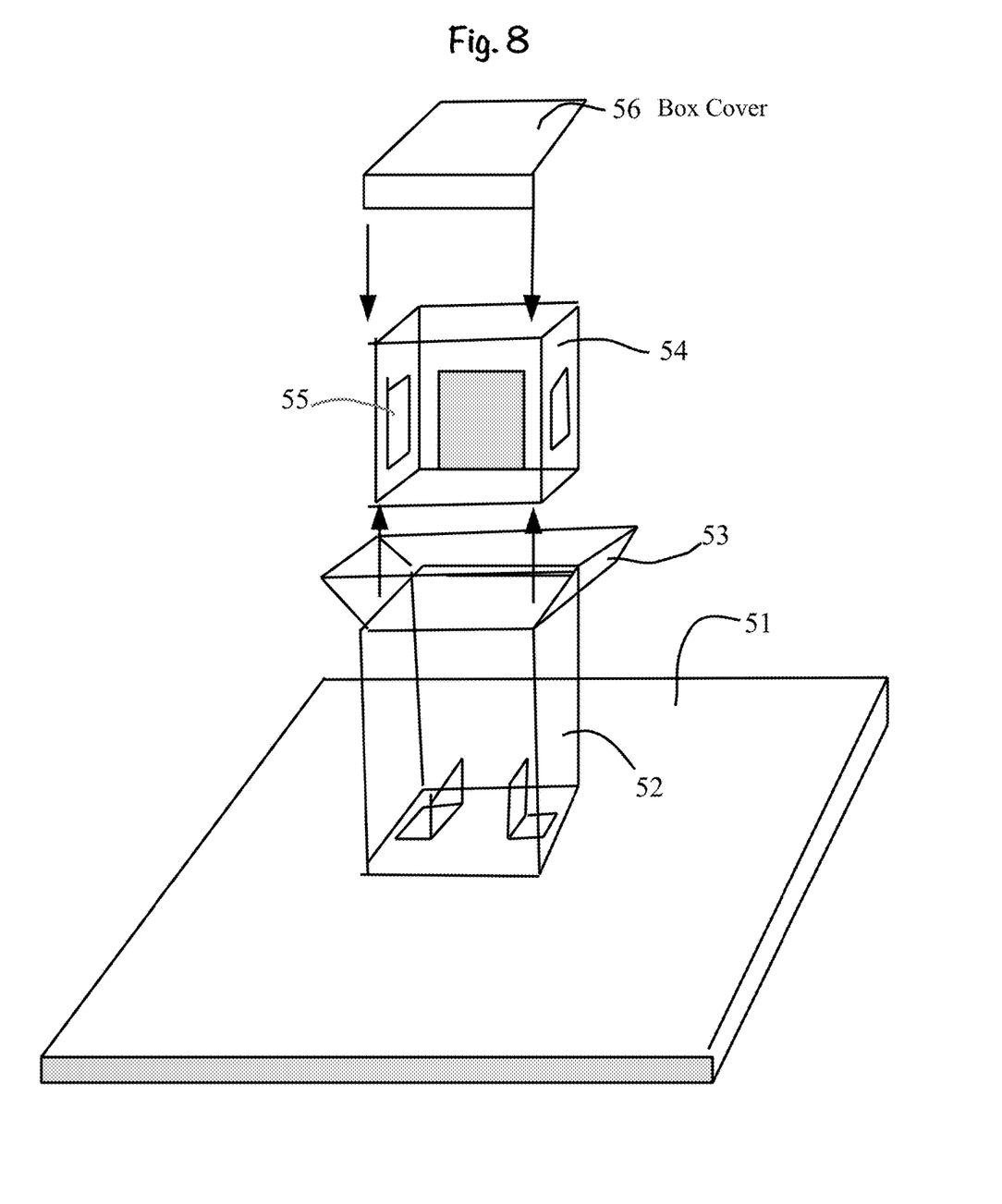
FIG. 8 is an exploded view of a restaurant table top shield.

Some of the most problematical locations in a pandemic are a restaurant, which is protected by an alternate embodiment of this invention shown in FIG. 8. The plexiglass restaurant shield is mounted in the center of table top 51 and comprises a box-like shield structure 52 with outwardly extending droplet deflectors 53 at its upper end. A purifier component box 54 fits inside the shield structure 52 and includes removable antimicrobial filters 55 and a top cover 56. The shield 50 can be incorporated in a centerpiece.

Figure 9:
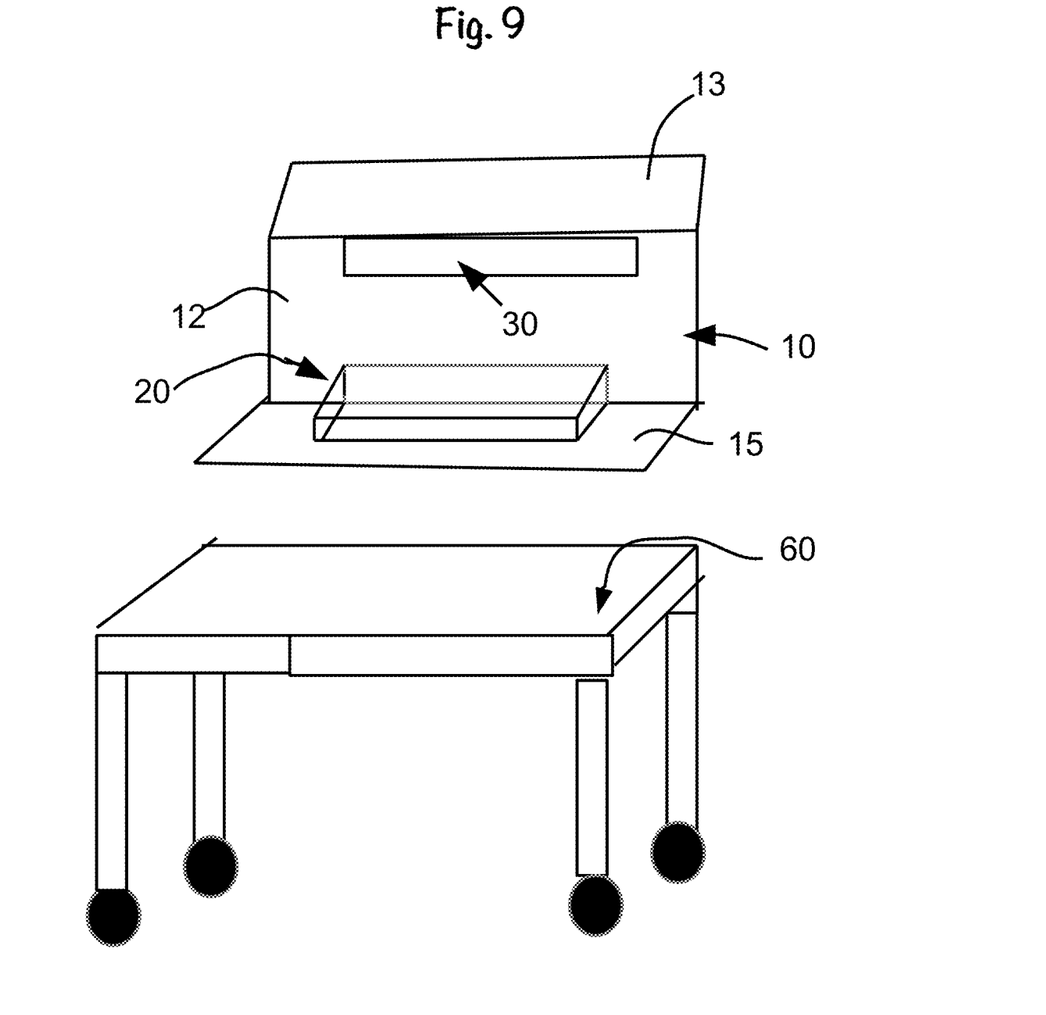
FIG. 9 discloses the invention in a schematic perspective view of a porta-shield adjustable height and width tablecart.

As disclosed in FIG. 9, the shield 10 of the present invention may be mounted on a portable and adjustable rolling cart 60. The width of the shield 10 can be custom made to fit 2, 3 or 4 individuals on the visitor side of the shield 10. The vertical plastic portion 12 includes an angled upper portion 13 and a hood 30 which has draft generating fans 31, a timer 33 and a motion sensor 32 incorporated therein as previously described. A purification filtration box 20 is mounted on the shield base 15 which is affixed to the cart 60 side wings 16a and 16b (not shown) are another option. This cart embodiment 60 is particularly useful in a hospital setting.

In summary, the in-filter 23 in the box 20 is a CoolVisions filter and the out-filter 26 will be a HEPA filter or equivalent. Both filters 23 and 26 will have UV-C light constantly shinning on them to disinfect. The filters 23 and 26 are replaceable and are infused with tourmaline and the Quaternary antimicrobial.

What is claimed is:

1. A pathogen containment shield mounted on a counter to protect both employees and customer from pathogen laden droplets or aerosols as a result of breathing, talking, coughing or sneezing comprising:
    a vertical plastic shield portion between the customer and employee having an upper angled portion extending from the vertical portion towards the customer and angled wings extending outwardly from the vertical portion towards the customer on both sides of the vertical portion and a base portion extending outwardly from the vertical portion towards the employee;
    a hood mounted to the upper portion of the vertical shield portion and extending outwardly beneath the angled upper portion, said hood including a fan to direct pathogen droplets downwardly; and,
    a filtration box mounted to the base of the vertical portion to receive downwardly directed droplets from the hood, said box including a filter and means within the box to greatly reduce the number of airborne pathogens.

2. A pathogen containment shield in accordance with claim 1 wherein
    the vertical shield portion includes a T-shaped slot at its lower portion and a base portion extending outwardly at a right angle from the vertical shield in the employee portion on the counter direction and being mounted to said counter; and,
    the filtration box extends through the slot with equal portions on each side of the slot.

3. A pathogen containment shield in accordance with claim 2, wherein
    the hood includes:
    a filter;
    at least one fan mounted therein to direct pathogen droplets downwardly towards the filtration box;
    a motion sensor mounted therein to detect the presence of a customer and activate the fans; and,
    a timer to deactivate the fans when a customer leaves.

4. A pathogen containment device in accordance with claim 1, wherein the filtration box extends through the slot in the vertical shield portion and is mounted substantially equally on each side thereof.

5. A pathogen containment shield in accordance with claim 3 wherein the filtration box includes a removable filter; and, a UV-C light to kill pathogens trapped in the filter.

6. A pathogen containment shield in accordance with claim 1 wherein the hood includes:

an upper intake register having a plurality of fins;

a drop-in removable tourmaline filter positioned beneath the register;

at least one fan mounted therein to create a downward draft;

a motion sensor to detect the presence of a customer and activate the fan;

a timer to deactivate the fan after the customer has left; and, an exhaust register to direct the droplets downwardly towards the filtration box.

7. A pathogen containment shield in accordance with claim 6, wherein the filtration box comprises:

a droplet intake register;

a drop in removable; tourmaline and antimicrobial infused filter positioned beneath the register;

a base unit positioned below the filter having a vacuum and pathogen killing means mounted therein; and, exhaust filters to direct the pathogen free air outwardly therefrom.

8. A pathogen containment shield in accordance with claim 1 wherein the pathogen killing means comprises of a UV-C light and tourmaline and antimicrobial infused HEPA filters.

9. A pathogen containment shield in accordance with claim 6, wherein:

the motion sensor activates the pathogen killing means.

10. A pathogen containment device in accordance with claim 1, wherein the plastic shield is plexiglass.

11. A pathogen containment shield in accordance with claim 1 further including a portable and adjustable cart having the base portion of the vertical shield portion mounted thereto.

* * * * *